United States Patent
Barnett et al.

(10) Patent No.: US 9,504,602 B2
(45) Date of Patent: Nov. 29, 2016

(54) HEATING PAD

(71) Applicants: Ralph Lipsey Barnett, Wilmette, IL (US); James R. Wingfield, Crystal Lake, IL (US)

(72) Inventors: Ralph Lipsey Barnett, Wilmette, IL (US); James R. Wingfield, Crystal Lake, IL (US)

(73) Assignee: Triodyne Safety Systems, L.L.C., Glenview, IL (US)

( * ) Notice: Subject to any disclaimer, the term of this patent is extended or adjusted under 35 U.S.C. 154(b) by 493 days.

(21) Appl. No.: 14/014,132

(22) Filed: Aug. 29, 2013

(65) Prior Publication Data

US 2014/0074196 A1  Mar. 13, 2014

Related U.S. Application Data

(60) Provisional application No. 61/694,642, filed on Aug. 29, 2012.

(51) Int. Cl.
*A61F 7/08* (2006.01)
*A61F 7/00* (2006.01)
*A61F 7/02* (2006.01)

(52) U.S. Cl.
CPC .................. *A61F 7/08* (2013.01); *A61F 7/007* (2013.01); *A61F 2007/0071* (2013.01); *A61F 2007/0086* (2013.01); *A61F 2007/0093* (2013.01); *A61F 2007/0095* (2013.01); *A61F 2007/0296* (2013.01)

(58) Field of Classification Search
CPC .. A61F 7/08; A61F 7/007; A61F 2007/0071; A61F 2007/0086; A61F 2007/0093; A61F 2007/0095; A61F 2007/0296
See application file for complete search history.

(56) References Cited

U.S. PATENT DOCUMENTS

| | | | |
|---|---|---|---|
| 4,638,436 A * | 1/1987 | Badger | A61N 7/02 600/549 |
| 5,432,322 A | 7/1995 | Ingram et al. | |
| 2006/0195168 A1* | 8/2006 | Dunbar | A61F 7/007 607/108 |
| 2007/0016271 A1* | 1/2007 | Hammond | A61F 7/007 607/96 |
| 2008/0053979 A1* | 3/2008 | Toya | A61F 7/007 219/201 |
| 2012/0279953 A1* | 11/2012 | Augustine | A61G 13/12 219/217 |

* cited by examiner

*Primary Examiner* — Joseph Stoklosa
*Assistant Examiner* — Nicole L Pobre
(74) *Attorney, Agent, or Firm* — Pauley Erickson & Kottis

(57) ABSTRACT

An improved heating pad which minimizes or eliminates skin burns due to improper uses in three ways: by monitoring an absolute temperature of each surface of the heating pad; by monitoring a temperature difference between each surface of the heating pad, where a small temperature difference indicates that both sides of the heating pad are covered; and by monitoring the duty cycle of a heating element, where a large off portion of the duty cycle indicates both sides of the heating pad are covered.

20 Claims, 2 Drawing Sheets

HEATING PAD

CROSS REFERENCE TO RELATED APPLICATION

This application claims priority to U.S. Provisional Patent Application 61/694,642, filed 29 Aug. 2012, and entitled "Safety Controls To Assure One Uncovered Heating Pad Face." This priority application is hereby incorporated by reference herein and made a part hereof, including but not limited to those portions which specifically appear hereinafter.

BACKGROUND OF THE INVENTION

Field of the Invention

This invention is directed to an improved electric heating pad which prevents burns resulting from improper use. More specifically, this invention is directed to an improved electric heating pad which monitors temperatures of surfaces of the heating pad and/or monitors a duty cycle of an internal thermostat to detect when the heating pad is covered.

Discussion of Related Art

Electric heating pads are used by many for pain relief and to improve local blood circulation. However, use of electric heating pads is also associated with severe dangers including shock/electrocution, fire, and skin burns.

Underwriters Laboratories Inc. (UL) has developed and promulgated design rules that effectively mitigated the dangers of shock/electrocution and fire. However, UL has not undertaken a technical program that addresses the skin burn problem. Nevertheless, many heating pad manufacturers have falsely represented that their compliance with UL standards has ameliorated the skin burn propensity of their pads.

For the most part, heating pad manufacturers have attempted minimize the danger of skin burn injuries with the use of on-product and in-manual warnings that have been promulgated by UL, the Food and Drug Administration (FDA), and Consumer Product Safety Commission (CPSC). For example Table 1 shows a typical on-product warning label for an electric heating pad.

TABLE 1

| DANGER |
|---|
| TO REDUCE THE RISK OF BURNS, ELECTRIC SHOCK, AND FIRE, THIS PRODUCT MUST BE USED IN ACCORDANCE WITH THE FOLLOWING INSTRUCTIONS: •BURNS CAN OCCUR REGARDLESS OF CONTROL SETTING, CHECK SKIN UNDER PAD FREQUENTLY. •DO NOT SIT ON, LEAN AGAINST, OR CRUSH PAD-AVOID SHARP FOLDS, ALWAYS PLACE PAD ON TOP OF AND NOT UNDER YOUR BODY. NEVER PLACE PAD BETWEEN YOURSELF AND CHAIR, SOFA, BED, OR PILLOW. •DO NOT USE WHILE SLEEPING. •DO NOT USE ON AN INFANT. •THIS PAD IS NOT TO BE USED ON OR BY AN INVALID, SLEEPING OR UNCONSCIOUS PERSON, OR A PERSON WITH POOR BLOOD CIRCULATION OR DIABETES UNLESS CAREFULLY ATTENDED. •DO NOT USE ON AREAS OF INSENSITIVE SKIN. •NEVER USE PAD WITHOUT THE CLOTH COVER IN PLACE. DO NOT USE PINS OR OTHER METALLIC MEANS TO FASTEN THIS PAD IN PLACE. •DO NOT USE IN OXYGEN ATMOSPHERE. •NEVER PULL THIS PAD BY THE POWER SUPPLY CORD. DO NOT USE |

TABLE 1-continued

| DANGER |
|---|
| THE POWER SUPPLY CORD AS A HANDLE. UNPLUG WHEN NOT IN USE. •DO NOT USE PAD WITH LINIMENT, SALVE, OR OINTMENT PREPARATIONS THAT CONTAIN HEAT-PRODUCING INGREDIENTS. SKIN BURNS COULD RESULT. •CAREFULLY EXAMINE INNER COVER BEFORE EACH USE. DISCARD THE PAD IF INNER COVER SHOWS ANY SIGN OF DETERIORATION. •READ AND FOLLOW ALL INSTRUCTIONS ON BOX OR PACKED WITH PAD BEFORE USING. |

However, use of warnings has failed to reduce the burn rate. In fact, the CPSC estimates that the annual number of skin burns due to electric heating pads has increased by 33.9% from 1600 in 1995 to 2142 in 2008. Furthermore, as the number of required admonitions increases, the effectiveness of the warnings decreases as users become overwhelmed reducing the warnings to an exercise in liability proofing.

Most skin burn accidents can be attributed to three reasonably foreseeable misuses of the pads:

1. Covering both faces of the pad—increasing contact temperature or heat transfer to the body.
2. Falling asleep during use—increasing exposure time.
3. Omitting the cloth cover—increasing both the contact temperature and the rate of heat energy transfer to the body.

Some manufacturers have eliminated the third improper use by eliminating removable covers and only including permanent covers with their heating pads. However, this approach fails to eliminate or minimize the first two improper uses.

Manufacturers have also attempted to minimize the second improper use by including a dead-man switch with their heating pads. A dead-man switch is a lever or button that must be continuously depressed to maintain operation of the pad. Should the user fall asleep during use, the user will release the dead-man switch shutting off the heating pad. However, some users have been known to circumvent the dead-man switch by tying down the dead-man switch thereby overriding the safety aspect of the dead-man switch. Other manufacturers have eliminated the dangers of users tying down dead-man switches with an on/off switch with a maximum heating time of 20 minutes. The on switch allows the user to restart the 20-minute timer any time by pushing the on button or end the session by pushing the off button. If the user falls asleep or forgets to press the off button, the built-in-timer will automatically shut the unit off for safety. However, neither the dead-man switch nor the on/off switch with an automatic timer address the first misuse identified above.

Accordingly, there is a need for an improved electric heating pad that eliminates exposure to extreme temperatures when both faces of the heating pad are covered.

SUMMARY OF THE INVENTION

A general object of the invention is to provide an improved electric heating pad which can eliminate or reduce the incident of burns due to both sides of the electric heating pad being covered during use.

Many incidents of skin burns from electric heating pads are due to consumers improperly using the heating pad by placing a cover over the heating pad and positioning the heating pad between the body and a furniture piece. Both of these improper uses confine all or most of the heat energy generated by heating elements to an area of application on the body increasing the quantity and rate of heat transfer into the body. Proper use of the heating pad requires a user to place one surface of the heating pad against a body surface that is to be treated and allowing the other surface of the heating pad to be exposed to the atmosphere. The reason for this is that the total rate of heat energy transfer out of the heating pad is divided such that only about half will be transferred into the body and the rest of the heat is converted or convected away from the open side. Covering both sides of the heating pad, one by the body and the opposite by a cover or furniture, can result in nearly all of heat energy generated by the heating pad to be transferred to the skin of the user which may result in skin burns.

The heating pad device of this invention seeks to prevent skin burns due to covering both sides of a heating pad by: monitoring an absolute temperature of each surface of the heating pad; monitoring a temperature difference between each surface of the heating pad, where a small temperature difference indicates that both sides of the heating pad are covered; and by monitoring the duty cycle of the heating element, where, when at steady state operation, a large off portion of the duty cycle indicates both sides of the heating pad are covered.

The general object of the invention can be attained, at least in part, through a heating pad device which includes a first thermocouple mounted to a first surface of the heating pad to measure a first surface temperature ($T_1$) of the heating pad and a second thermocouple mounted to a second surface of the heating pad to measure a second surface temperature ($T_2$) of the heating pad. For ease of explanation, the first surface is understood to be a surface of the heating pad which is positioned adjacent to a surface of a body and the second surface is a surface of the heating pad which faces away from the surface of a body. However, the first surface may or may not be any different from the second surface. The heating pad device of this invention further includes a processor, such as a programmable logic controller, which can monitor temperature readings of both the first surface and the second surface of the heating pad as well as monitor a heating duty cycle of a heating element of the heating pad.

In operation, the processor receives the first surface temperature ($T_1$) and the second surface temperature ($T_2$). If either temperature exceeds a maximum temperature ($T_{max}$) the processor shuts off the heating pad. In a preferred embodiment, the maximum temperature ($T_{max}$) is variable and decreases the longer the heating pad stays on to prevent burns due to prolonged exposure and relatively lower temperatures. The processor also calculates a temperature difference ($T_{diff}=T_1-T_2$) between the first surface temperature ($T_1$) and the second surface temperature ($T_2$). If the processor detects a temperature difference ($T_{diff}=T_1-T_2$) that is less than a minimum temperature difference ($T_{diff,min}$) the processor shuts off the heating pad. When the temperature difference ($T_{diff}=T_1-T_2$) is less than a minimum temperature difference ($T_{diff,min}$) it indicates that both surfaces of the heating pad are covered.

In operation, the processor also receives the heating duty cycle ($\tau$) of the heating element. The heating duty cycle ($\tau$) comprises a repeating period which includes an on portion where the heating element receives current and heating the element up and an off portion where the heating element does not receive current. The processor monitors the duty cycle to calculate a ratio that the heating pad is off ($R_{off}$), $$R_{off} = \frac{t_{off}}{t_{on}+t_{off}} = \frac{t_{off}}{\tau},$$

where $t_{off}$ is the portion of the duty cycle the heating element is off and $t_{on}$ is the portion of the duty cycle the heating element is on. When the processor calculates the $R_{off}$ as greater than a maximum allowable ratio ($R_{off,max}$), indicating that both surfaces of the heating pad are covered, the programmable logic controller shuts off the heating pad to prevent burns.

In a preferred embodiment, the heating pad of this invention further includes a permanently attached cover to prevent burns due to users using the heating pad without a cover and a switch, such as a dead-man switch and a timed switch, to prevent burns due to users falling asleep during use.

BRIEF DESCRIPTION OF THE DRAWINGS

These and other objects and features of this invention will be better understood from the following detailed description taken in conjunction with the drawings, wherein.

DESCRIPTION OF PREFERRED EMBODIMENTS

Figure 1:
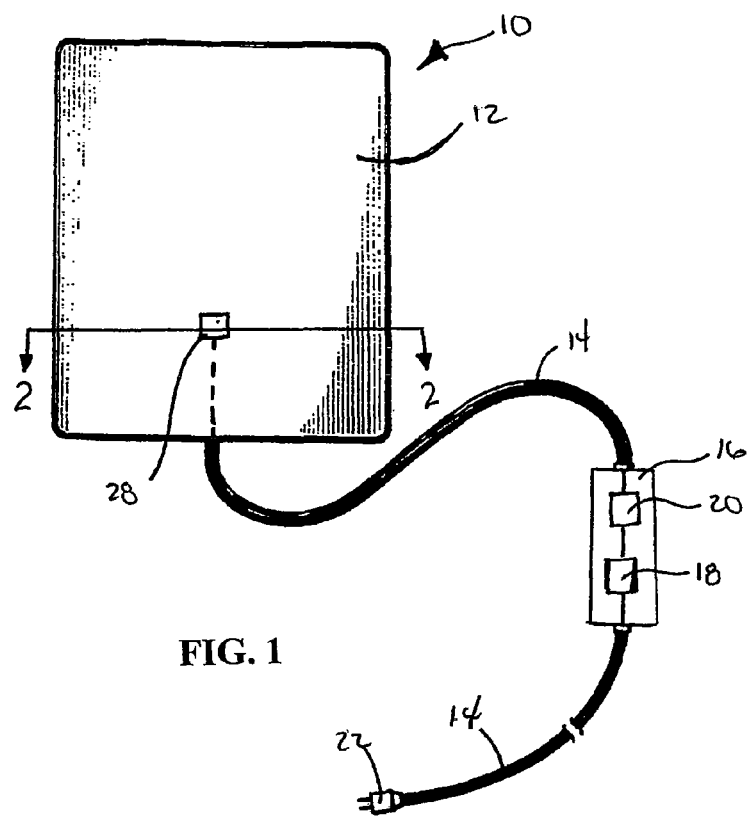
FIG. 1 is a top view of the electric heating pad according to an embodiment of this invention.
Figure 2:
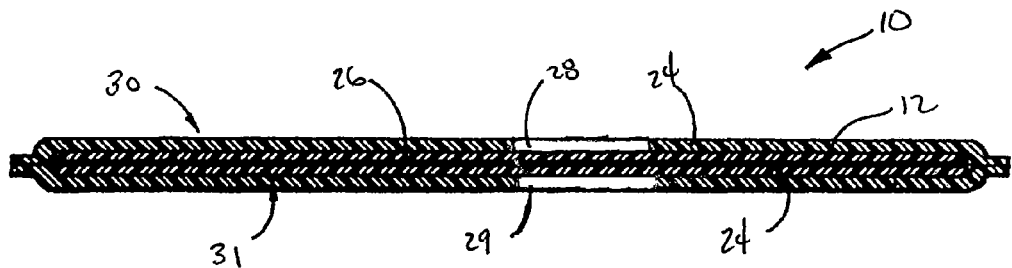
FIG. 2 is a cross-sectional view of the electric heating pad of FIG. 1.

FIGS. 1 and 2 show a preferred embodiment of an electric heating pad 10 of this invention which can eliminate or reduce skins burns by detecting when both sides of the electric heating pad are covered and shutting off the device.

The electric heating pad 10 of this invention seeks to prevent skin burns by: monitoring an absolute temperature of each surface of the heating pad 10; monitoring a temperature difference between each surface of the heating pad 10, where a small temperature difference indicates that both sides of the heating pad 10 are covered; and by monitoring a duty cycle of the heating pad 10, where a large off portion of the duty cycle indicates both sides of the heating pad 10 are covered.

As shown in FIGS. 1 and 2, the electric heating pad 10 according to an embodiment of this invention comprises a pad 12, a cord 14, a control box 16 including an on/off switch 18 and a processor 20, and a plug 22. The processor 20 preferably comprises a programmable logic controller. The pad 12 preferably includes a cover 24 surrounding a heating element 26. In this embodiment, the pad 12 is generally planar with a square-shape, usefully for application on, for example, a patient's back or legs. However, the pad 12 need not be planar and square-shaped and may comprise any shape and be non-planar to fit around a joint, for example, a patient's knee. In this embodiment, the covering 24 comprises polymer sub-layer with a cloth outer layer which provides a flexible device which can conform to a part while the cloth cover provides insulation from the heating element to prevent burns. However, it should be understood that the pad may be constructed of any material known in the art such as, but not limited to, vinyl, PVC, rubber, felt, polymer and composite materials. Preferably, the cover is permanently attached to the heating pad 10.

As best shown in FIG. 2, the pad 12 further comprises a pair of thermocouples 28, 29 adjacent to a first surface 30 of the pad 12 and a second surface 31 of the pad 12. The pair of thermocouples 28, 29 are electrically connected to the programmable logic controller to measure a temperature of the first surface 30 and the second surface 31. In an alternative embodiment, another device known to one of skill in the art may be used to measure the temperature of the surfaces 30, 31 of the pad 12. In the embodiment of FIG. 2, the thermocouples 28, 29 are integrated with the cover 24. Alternatively, the thermocouples may be integrated with the heating element 26 or mounted to a surface of the cover 24.

In operation, the processor 20 receives the first surface temperature ($T_1$) from the first thermocouple 28 and the second surface temperature ($T_2$) from the second thermocouple 29. If either temperature exceeds a maximum temperature ($T_{max}$) the processor 20 shuts off the heating element 26. In a preferred embodiment, the maximum temperature ($T_{max}$) is specified. The maximum temperature can be set in the processor to act as a limiting operating temperature monitor and back up possible internal control thermostats malfunction.

The processor 20 also calculates a temperature difference ($T_{diff}=T_1-T_2$) between the first surface 30 temperature ($T_1$) and the second surface 31 temperature ($T_2$). If the processor detects a temperature difference ($T_{diff}=T_1-T_2$) that is less than a minimum temperature difference ($T_{diff,min}$) the programmable logic controller 20 shuts off the heating element 26. When the temperature difference ($T_{diff}=T_1-T_2$) is less than a minimum temperature difference ($T_{diff,min}$) it indicates that both surfaces 30, 31 of the heating pad 10 are covered. The minimum temperature difference ($T_{diff,min}$) can vary greatly depending on the design of the heating pad 10 and can, for example, be selected to vary from 1° F. to 30° F. or more. In an embodiment of this invention, the minimum temperature difference ($T_{diff,min}$) was selected to be 6° F. to initiate a shutdown of the heating element.

In a preferred embodiment, the processor 20 receives the heating duty cycle ($\tau$) of the heating element 26. The heating duty cycle ($\tau$) comprises a repeating period which includes an on portion where the heating element 26 receives current and heating the element up and an off portion where the heating element 26 does not receive current. The processor 20 monitors the duty cycle to calculate a ratio that the heating pad is off ($R_{off}$), $$R_{off} = \frac{t_{off}}{t_{on}+t_{off}} = \frac{t_{off}}{\tau},$$

where $t_{off}$ is the portion of the duty cycle the heating element 26 is off and $t_{on}$ is the portion of the duty cycle the heating element 26 is on. When the processor 20 calculates the $R_{off}$ as greater than a maximum allowable ratio ($R_{off,\,max}$), indicating that both surfaces 30, 31 of the heating pad 10 are covered, the processor 20 shuts off the heating element 26 to prevent burns. The maximum allowable ratio ($R_{off,\,max}$) can vary greatly depending on the design of the heating pad 10 and can, for example, be selected to vary from 0.30 to 0.90. In an embodiment of this invention, the maximum allowable ratio ($R_{off,\,max}$) was selected to be 0.70 to initiate a shutdown of the heating element. In a preferred embodiment, the $R_{off}$ is calculated as an average of a plurality of duty cycles to compensate for fluctuations in the duty cycle. In an alternative embodiment, the processor of this invention may monitor the ratio that the heating pad is off ($R_{off}$) to detect a change in the $R_{off}$ over a period of time ($\Delta R_{off}$). When the processor detects a change exceeding a set limit ($\Delta R_{off,\,max}$), the processor shuts off the heating element to prevent skin burns. The maximum allowable change in the $R_{off}$ over a period of time ($\Delta R_{off,\,max}$) can vary greatly depending on the design of the heating pad 10 and can, for example, be selected to range from 0.01 change to 0.20 change or more. In an embodiment of this invention, the maximum allowable change in the $R_{off}$ over a period of time ($\Delta R_{off}$) was selected to be 0.07, or approximately a 12% change in $R_{off}$, to initiate a shutdown of the heating element.

In a preferred embodiment, the heating pad 10 further includes either a dead-man switch or a timed switch to prevent burns due to users falling asleep during use.

Experiment

Surface Temperatures

Covering both sides of a pad during therapy causes the temperature and heat transfer at the interface between the heating pad and the body to increase to dangerous levels. In this experiment, a heating pad, a model HP-110 heating pad manufactured by KAZ, Inc., was tested for 120 minutes at the high control setting. A pair of K-type thermocouples were attached at the geometric center of vinyl faces of the heating pad. The experiment was conducted by placing the test pad on top of an application surface that roughly approximated the behavior of a human body. The temperature of application surface was measured to be 88° F., about 6° F. cooler than a human body surface temperature of 94° F.

The temperature measured by the thermocouple in contact with the application surface was designated $T_1$ and the other thermocouple temperature was designated $T_2$. With the test pad set on high and the top surface exposed to the environment, the temperatures $T_1$ and $T_2$ were monitored for 60 minutes; the values are tabulated in Table 2.

TABLE 2

| Time (min.) | Body Side $T_1$(° F.) | Top Side $T_2$(° F.) |
|---|---|---|
| 0 | 72.9 | 72.8 |
| 5 | 142.0 | 130.7 |
| 10 | 150.9 | 127.6 |
| 15 | 142.1 | 122.1 |
| 20 | 140.0 | 121.2 |
| 25 | 139.4 | 120.9 |
| 30 | 138.9 | 119.6 |
| 35 | 139.0 | 119.4 |
| 40 | 138.8 | 180.0 |
| 45 | 139.1 | 119.7 |
| 50 | 139.2 | 120.0 |
| 55 | 138.6 | 119.4 |

At the end of the first 60 minute interval, the top surface of the test pad was covered with a ½ inch thick felt pad and monitored for an additional 60 minutes until completion of a two hour test run. The temperatures $T_1$ and $T_2$ associated with this insulated phase of the testing program are displayed in Table 3.

TABLE 3

| Time (min.) | Body Side $T_1$(° F.) | Top Side $T_2$(° F.) |
|---|---|---|
| 60 | 139.4 | 121.2 |
| 65 | 140.0 | 126.5 |
| 70 | 141.3 | 132.4 |
| 75 | 142.4 | 132.6 |
| 80 | 141.6 | 136.4 |
| 85 | 141.9 | 137.6 |
| 90 | 141.8 | 138.3 |
| 95 | 141.6 | 138.2 |
| 100 | 141.4 | 138.2 |
| 105 | 141.4 | 139.7 |
| 110 | 141.3 | 138.1 |
| 115 | 141.1 | 138.1 |
| 120 | 142.3 | 139.1 |

Figure 3:
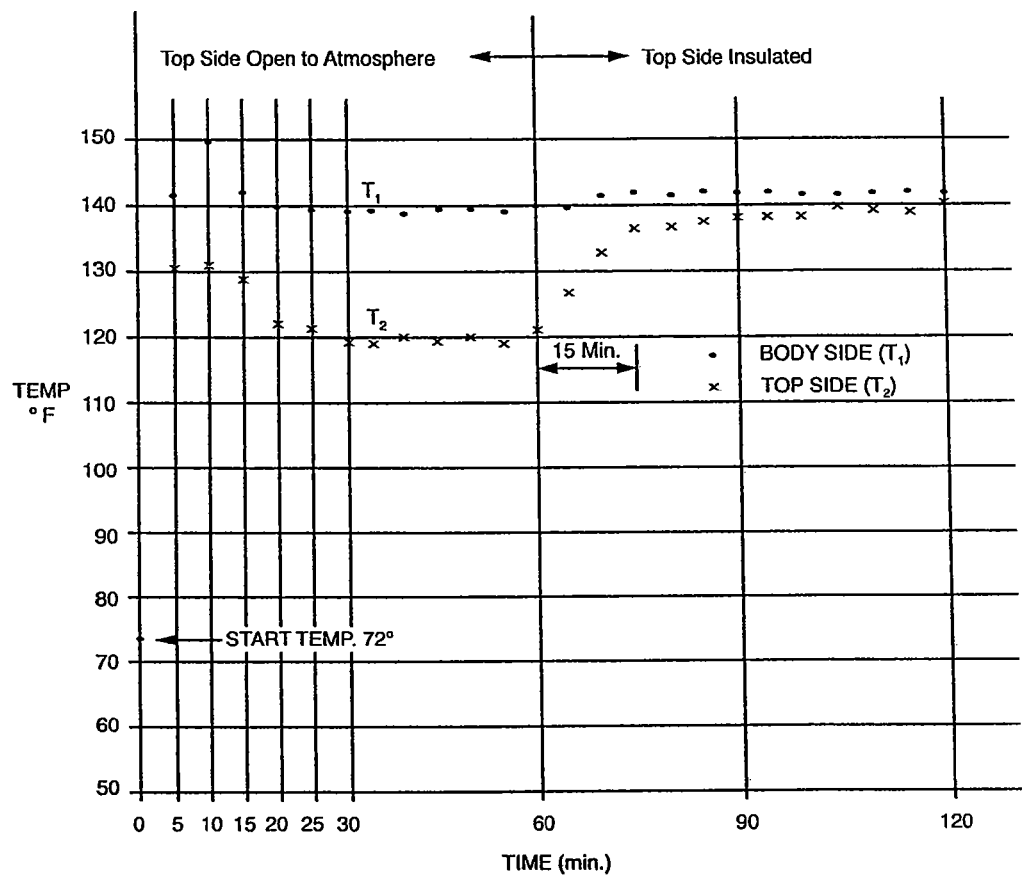
FIG. 3 is a graph showing experimental data of surface temperatures of a heating pad in an uncovered and covered state.

The results of the testing program are summarized in FIG. 3. The following observations are noteworthy:
a. Top side open to atmosphere
   i. The start-up temperature was 72° F.
   ii. In the first 10 minutes, $T_1$ overshoots to about 150° F. before returning to a steady state temperature of 138° F.
   iii. $T_1$ remained steady at 138° for about 50 minutes.
   iv. The temperature $T_2$ exhibits a similar response, overshoots to about 130° F. and returns to a steady state of about 118° F. for the next 40 minutes.
   v. The programmable logic controller (PLC) recorded a steady state temperature difference ($T_1-T_2$) of 20° F. when the test pad had its top side open to the atmosphere.
b. Top side insulated
   i. After 60 minutes the top side of the test pad was insulated with a felt pad.
   ii. Over the next 15 minutes, $T_1$ rose from 138° F. to 142° F.
   iii. Within 15 minutes, $T_2$ rose from 118° F. to 136° F.
   iv. Over the next 40 minutes $T_1$ is stable and $T_2$ gradually increases to within 5° to 6° F. of $T_1$.

From this data, the PLC recorded that the initial steady state difference ($T_1-T_2$) of 20° F. becomes a 6° F. difference in 15 minutes when the top side is covered. This change in ($T_1-T_2$) reflects the physical application of an insulated cover of the top side. Using this data, a heating pad can be designed to shut off the heating element to prevent burns when the ($T_1-T_2$) is less than 7° F. to protect the user from this "covering misuse."

Further, using this data, the heating pad can be designed to provide an additional layer of protection, the PLC can shut off the heating pad when the $T_1$ exceeds, for example, 140° F., as an emergency measure.

Experiment

Duty Cycle Control

A heating element will draw more energy to maintain a steady state heating pad temperature when one face of the pad is uncovered because some energy is expended to the environment. Consequently, the on/off electrical demand spends more time in the "on" state when a heating pad face is uncovered as opposed to covered. If the average heating times are stable and significantly different in the covered and uncovered states, a small difference in the average heating time provides a criterion for shutting off the heating pad before skin burns occur. No additional hardware, thermocouples, or wiring is required. Only control logic and monitoring activities are incorporated to provide a primary or secondary safety system.

In this experiment, the PLC was programmed to measure the period of an on/off duty cycle. The duty cycle period ($\tau$) of this type of control is the sum of time on ($t_{on}$) plus time off ($t_{off}$), $\tau = t_{on} + t_{off}$. The duty cycle is a stochastic variable so in this experiment an average of ten cycles was used to describe this period. Using this cycle period, a ratio $\bar{R}_{off}$ was then defined as $$\bar{R}_{off} = \frac{\bar{t}_{off}}{\bar{t}_{on} + \bar{t}_{off}} = \frac{\bar{t}_{off}}{\tau},$$

where the over bar symbol denotes an average.

Using the same set up described above in the previous experiment, a two hour test run was undertaken to study the duty cycles with the heating pad in the uncovered and covered states. The test protocol is characterized as follows:
   i. The test pad was set on high and placed onto the application surface.
   ii. For various 5 minute intervals, ten values of $t_{on}$ and $t_{off}$ were measured with the top surface of the heating pad open to the atmosphere.
   iii. Step (ii) was then repeated with the top surface covered with a felt pad.
   iv. The felt pad was then removed and, after a delay, step (ii) was repeated.

The observed duty cycle data is tabulated in Table 4.

TABLE 4

| Run Time (min.) | $\bar{t}_{on}$ | $\bar{t}_{off}$ | $\bar{R}_{off}$ | Cover |
|---|---|---|---|---|
| 5-10 | 6.9 | 13.8 | 0.666 | Off |
| 10-15 | 9.5 | 15.3 | 0.610 | Off |
| 15-20 | 10.6 | 16.9 | 0.614 | Off |
| 20-25 | 12.5 | 20.3 | 0.618 | Off |
| 25-30 | 16.1 | 23.4 |  | Off |
| 60-65 | 16.5 | 24.9 | 0.600 | On |
| 65-70 | 15.7 | 31.0 | 0.664 | On |
| 70-75 | 17.0 | 40.2 | 0.702 | On |
| 75-80 | 14.7 | 39.9 | 0.730 | On |
| 85-90 | 16.6 | 40.0 | 0.709 | On |
| 90-95 | 17.0 | 47.9 | 0.738 | On |
| 95-100 | 15.1 | 52.8 | 0.777 | On |
| 110-115 | 18.6 | 33.7 | 0.644 | Off |
| 115-120 | 21.5 | 35.0 | 0.619 | Off |

From the data in Table 4, the mean value of the seven averages for $R_{off}$ associated with the uncovered test pad is 0.6230. The corresponding mean of seven averages $R_{off}$ for the covered test pad is 0.7029. Covered $R_{off}$-Uncovered $R_{off}$=0.0799. The inactive time $t_{off}$ increased 12.83% when the heating pad was covered. Using this data, a heating pad can be designed to shut off the heating element to prevent burns when the $R_{off}$ exceeds 0.700 or when the change in $R_{off}$ exceeds 12%

Thus, the invention provides an improved heating pad which includes a pair of thermocouples and a processor to prevent skin burns due to covering both sides of a heating pad by: monitoring an absolute temperature of each surface of the heating pad; monitoring a temperature difference between each surface of the heating pad, where a small temperature difference indicates that both sides of the heating pad are covered; and by monitoring the duty cycle of the heating element, where a large off portion of the duty cycle indicates both sides of the heating pad are covered.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A method of monitoring a heating pad to prevent skin burns comprising:
   measuring a first surface temperature ($T_1$) of the heating pad, wherein the first surface is a surface of the heating pad which is positioned adjacent to a surface of a body;
   measuring a second surface temperature ($T_2$) of the heating pad, wherein the second surface faces away from the surface of the body; and
   automatically determining if the second surface is improperly covered by comparing the first surface temperature ($T_1$) and the second surface temperature ($T_2$), wherein when a temperature difference ($T_{diff} = T_1 - T_2$) is less than a minimum temperature difference ($T_{diff,min}$) the heating pad shuts off.

2. The method of claim 1, wherein the minimum temperature difference ($T_{diff,min}$) equals approximately 6° F.

3. The method of claim 1, wherein when the first surface temperature ($T_1$) exceeds a maximum temperature ($T_{max}$) the heating pad shuts off.

4. The method of claim 3, wherein the maximum temperature ($T_{max}$) varies based on an amount of time the heating pad has been on.

5. The method of claim 1, wherein the heating pad includes a dead-man switch, wherein the dead-man switch must be depressed for the heating pad to heat up.

6. The method of claim 1, wherein the heating pad includes a timer switch, wherein the timer switch turns on the heating pad for a set period of time.

7. The method of claim 1 further comprising:
   monitoring a duty cycle ($\tau$), wherein the duty cycle ($\tau$) comprises a period of time a heating element is on ($t_{on}$) and a time the heating element is off ($t_{off}$);
   calculating a ratio the heating pad is off ($R_{off}$) per period using $$R_{off} = \frac{t_{off}}{t_{on} + t_{off}} = \frac{t_{off}}{\tau};$$

and
   turning off the heating pad when the ratio the heating pad is off ($R_{off}$) is greater than a maximum ratio ($R_{off, max}$).

8. The method of claim 7, wherein the ratio the heating pad is off is calculated as an average over a plurality of periods.

9. The method of claim 7, wherein the maximum ratio ($R_{off, max}$) is approximately 0.7.

10. A method of monitoring a heating pad to prevent skin burns comprising:
    monitoring a duty cycle ($\tau$), wherein the duty cycle ($\tau$) comprises a period of time a heating element is on ($t_{on}$) and a time the heating element is off ($t_{off}$);
    calculating a ratio the heating pad is off ($R_{off}$) per period using $$R_{off} = \frac{t_{off}}{t_{on} + t_{off}} = \frac{t_{off}}{\tau};$$

and
    turning off the heating pad when the ratio the heating pad is off ($R_{off}$) is greater than a maximum ratio ($R_{off, max}$).

11. The method of claim 10, wherein the ratio the heating pad is off is calculated as an average over a plurality of periods.

12. The method of claim 7, wherein the heating pad includes a dead-man switch, wherein the dead-man switch must be depressed for the heating pad to heat up.

13. The method of claim 7, wherein the heating pad includes a timer switch, wherein the timer switch turns on the heating pad for a set period of time.

14. The method of claim 7 further including:
    measuring a first surface temperature ($T_1$) of the heating pad, wherein the first surface is a surface of the heating pad which is positioned adjacent to a surface of a body; and
    wherein when the first surface temperature ($T_1$) exceeds a maximum temperature ($T_{max}$) the heating pad shuts off.

15. The method of claim 14, wherein the maximum temperature ($T_{max}$) is variable based on an amount of time the heating pad has been on.

16. The method of claim 1, wherein:
    a first thermocouple is mounted to the first surface of the heating pad to measure the first surface temperature ($T_1$) of the heating pad;
    a second thermocouple is mounted to the second surface of the heating pad to measure the second surface temperature ($T_2$) of the heating pad; and
    a processor compares the first surface temperature ($T_1$) and the second surface temperature ($T_2$), wherein when the processor detects the temperature difference ($T_{diff} = T_1 - T_2$) that is less than the minimum temperature difference ($T_{diff,min}$) the processor shuts off the heating pad.

17. The method of claim 16, wherein the processor comprises a programmable logic controller.

18. The method of claim 17, wherein the programmable logic controller shuts off the heating pad when the first surface temperature ($T_1$) exceeds a maximum temperature ($T_{max}$).

19. The method of claim 18, wherein the maximum temperature ($T_{max}$) is variable based on an amount of time the heating pad has been on.

20. The method of claim 17, wherein the programmable logic controller monitors a duty cycle of the heating pad and turns off the heating pad when a ratio the heating pad is off ($R_{off}$) is greater than a maximum allowable ratio ($R_{off, max}$), wherein a duty cycle period ($\tau$) is a sum of a time the heating pad is on ($t_{on}$) plus a time the heating pad is off ($t_{off}$) and the ratio the heating pad is off ($R_{off}$) is equal to $$R_{off} = \frac{t_{off}}{t_{on} + t_{off}} = \frac{t_{off}}{\tau}.$$

* * * * *